(12) United States Patent
Vitaris et al.

(10) Patent No.: US 8,021,347 B2
(45) Date of Patent: Sep. 20, 2011

(54) THIN FILM WOUND DRESSING

(75) Inventors: Ronald F. Vitaris, Worcester, MA (US);
Rose Anderson, Melrose, MA (US);
Deirdre McKeown, Boston, MA (US);
Adam M. Ruggles, Chicago, IL (US)

(73) Assignee: Tyco Healthcare Group LP, Mansfield, MA (US)

( * ) Notice: Subject to any disclaimer, the term of this patent is extended or adjusted under 35 U.S.C. 154(b) by 407 days.

(21) Appl. No.: 12/176,773

(22) Filed: Jul. 21, 2008

(65) Prior Publication Data

US 2010/0016815 A1 Jan. 21, 2010

(51) Int. Cl.
*A61F 13/00* (2006.01)
*A61F 15/00* (2006.01)
*A61M 1/00* (2006.01)
*A61M 27/00* (2006.01)

(52) U.S. Cl. ......... 604/304; 604/313; 604/543; 602/52; 602/57

(58) Field of Classification Search .......... 604/304, 604/313, 543
See application file for complete search history.

(56) References Cited

U.S. PATENT DOCUMENTS

| | | |
|---|---|---|
| 3,026,874 A | 3/1962 | Stevens |
| 3,367,332 A | 2/1968 | Groves |
| 3,486,504 A | 12/1969 | Austin, Jr. |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,202,331 A | 5/1980 | Yale |
| 4,224,945 A | 9/1980 | Cohen |
| 4,228,798 A | 10/1980 | Deaton |
| 4,266,545 A | 5/1981 | Moss |

(Continued)

FOREIGN PATENT DOCUMENTS

DE 41 11 122 A1 4/1993

(Continued)

OTHER PUBLICATIONS

Björn, et al., "Irrigation Treatment in Split-thickness Skin Grafting of Intractable Leg Ulcers," Scand J Plast Reconstr Surg 19: 211-213, 1985.

(Continued)

*Primary Examiner* — Leslie Deak
*Assistant Examiner* — Susan Su
(74) *Attorney, Agent, or Firm* — Elias Domingo, Esq.

(57) ABSTRACT

A composite wound dressing and delivery apparatus includes a substantially transparent dressing layer having a lower surface that is coated with a pressure sensitive for applying the dressing layer over a wound to define a reservoir in which a negative pressure may be maintained. A substantially transparent backing layer adhered to the lower surface of the dressing layer in a releasable manner, and a vacuum port is centrally located on the dressing layer. The vacuum port is adapted to provide fluid communication between a vacuum source and the reservoir through the dressing layer. A targeting grid associated with either the dressing layer or the backing layer includes regularly spaced reference marks along at least two axes extending from the vacuum port.

10 Claims, 7 Drawing Sheets

U.S. PATENT DOCUMENTS

| | | | |
|---|---|---|---|
| 4,280,680 A | 7/1981 | Payne | |
| 4,382,441 A | 5/1983 | Svedman | |
| 4,499,896 A * | 2/1985 | Heinecke | 602/47 |
| 4,510,802 A | 4/1985 | Peters | |
| 4,524,064 A | 6/1985 | Nambu | |
| 4,538,645 A | 9/1985 | Perach | |
| 4,600,001 A * | 7/1986 | Gilman | 602/52 |
| 4,655,754 A | 4/1987 | Richmond et al. | |
| 4,700,479 A | 10/1987 | Saito et al. | |
| 4,710,165 A | 12/1987 | McNeil et al. | |
| 4,738,257 A | 4/1988 | Meyer et al. | |
| 4,743,232 A | 5/1988 | Kruger | |
| 4,786,282 A * | 11/1988 | Wagle et al. | 604/307 |
| 4,870,975 A | 10/1989 | Cronk et al. | |
| 4,874,363 A | 10/1989 | Abell | |
| 4,917,112 A * | 4/1990 | Kalt | 602/58 |
| 4,969,880 A | 11/1990 | Zamierowski | |
| 4,984,570 A * | 1/1991 | Langen et al. | 602/44 |
| 4,990,137 A | 2/1991 | Graham | |
| 4,997,438 A | 3/1991 | Nipper | |
| 5,000,172 A * | 3/1991 | Ward | 602/52 |
| 5,059,424 A * | 10/1991 | Cartmell et al. | 424/443 |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,135,485 A | 8/1992 | Cohen et al. | |
| 5,141,503 A | 8/1992 | Sewell, Jr. | |
| 5,149,331 A | 9/1992 | Ferdman et al. | |
| 5,152,757 A | 10/1992 | Eriksson | |
| 5,160,322 A | 11/1992 | Scheremet et al. | |
| 5,176,663 A | 1/1993 | Svedman et al. | |
| 5,178,157 A | 1/1993 | Fanlo | |
| 5,180,375 A | 1/1993 | Feibus | |
| 5,195,977 A | 3/1993 | Pollitt | |
| 5,261,893 A | 11/1993 | Zamierowski | |
| 5,263,922 A | 11/1993 | Sova et al. | |
| 5,265,605 A * | 11/1993 | Afflerbach | 600/300 |
| 5,415,627 A | 5/1995 | Rasmussen et al. | |
| 5,423,737 A * | 6/1995 | Cartmell et al. | 602/57 |
| 5,447,492 A * | 9/1995 | Cartmell et al. | 602/58 |
| D364,679 S | 11/1995 | Heaton et al. | |
| 5,484,427 A | 1/1996 | Gibbons | |
| 5,489,262 A * | 2/1996 | Cartmell et al. | 602/57 |
| 5,527,293 A | 6/1996 | Zamierowski | |
| 5,536,233 A | 7/1996 | Khouri | |
| 5,549,584 A | 8/1996 | Gross | |
| 5,588,958 A | 12/1996 | Cunningham et al. | |
| 5,605,165 A * | 2/1997 | Sessions et al. | 128/888 |
| 5,624,374 A | 4/1997 | Von Iderstein | |
| 5,636,643 A | 6/1997 | Argenta et al. | |
| 5,645,081 A | 7/1997 | Argenta et al. | |
| 5,678,564 A | 10/1997 | Lawrence et al. | |
| 5,701,917 A | 12/1997 | Khouri | |
| 5,704,905 A | 1/1998 | Jensen et al. | |
| 5,713,842 A * | 2/1998 | Kay | 602/57 |
| 5,733,305 A | 3/1998 | Fleischmann | |
| 5,738,642 A * | 4/1998 | Heinecke et al. | 602/58 |
| 5,749,842 A * | 5/1998 | Cheong et al. | 602/41 |
| 5,779,657 A | 7/1998 | Daneshvar | |
| 5,840,049 A | 11/1998 | Tumey et al. | |
| 5,911,222 A | 6/1999 | Lawrence et al. | |
| 5,931,800 A * | 8/1999 | Rasmussen et al. | 602/57 |
| 5,944,703 A | 8/1999 | Dixon et al. | |
| 5,960,837 A | 10/1999 | Cude | |
| 5,973,221 A * | 10/1999 | Collyer et al. | 602/46 |
| 6,010,524 A | 1/2000 | Fleischmann | |
| 6,043,406 A * | 3/2000 | Sessions et al. | 602/41 |
| 6,071,267 A | 6/2000 | Zamierowski | |
| 6,093,465 A * | 7/2000 | Gilchrist et al. | 428/40.1 |
| 6,117,111 A | 9/2000 | Fleischmann | |
| 6,135,116 A | 10/2000 | Vogel et al. | |
| D434,150 S | 11/2000 | Tumey et al. | |
| 6,142,982 A | 11/2000 | Hunt et al. | |
| 6,168,800 B1 * | 1/2001 | Dobos et al. | 424/405 |
| 6,174,306 B1 | 1/2001 | Fleischmann | |
| 6,203,563 B1 | 3/2001 | Fernandez | |
| 6,261,276 B1 | 7/2001 | Reitsma | |
| 6,325,788 B1 | 12/2001 | McKay | |
| 6,345,623 B1 | 2/2002 | Heaton et al. | |
| 6,348,423 B1 | 2/2002 | Griffiths et al. | |
| 6,395,955 B1 | 5/2002 | Roe et al. | |
| 6,398,767 B1 | 6/2002 | Fleischmann | |
| 6,406,447 B1 | 6/2002 | Thrash et al. | |
| 6,420,622 B1 | 7/2002 | Johnston et al. | |
| 6,458,109 B1 | 10/2002 | Henley et al. | |
| 6,488,643 B1 | 12/2002 | Tumey et al. | |
| 6,500,112 B1 | 12/2002 | Khouri | |
| D469,175 S | 1/2003 | Hall et al. | |
| D469,176 S | 1/2003 | Hall et al. | |
| 6,520,982 B1 | 2/2003 | Boynton et al. | |
| 6,547,255 B1 | 4/2003 | Donaway et al. | |
| 6,553,998 B2 | 4/2003 | Heaton et al. | |
| D475,134 S | 5/2003 | Randolph | |
| 6,557,704 B1 | 5/2003 | Randolph | |
| D478,659 S | 8/2003 | Hall et al. | |
| 6,607,495 B1 | 8/2003 | Skalak et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| D488,558 S | 4/2004 | Hall | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,855,860 B2 | 2/2005 | Ruszczak et al. | |
| 6,856,821 B2 | 2/2005 | Johnson | |
| 6,887,228 B2 | 5/2005 | McKay | |
| 6,887,263 B2 | 5/2005 | Bleam et al. | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,960,181 B2 | 11/2005 | Stevens | |
| 6,979,324 B2 | 12/2005 | Bybordi et al. | |
| 6,994,702 B1 | 2/2006 | Johnson | |
| 7,022,113 B2 | 4/2006 | Lockwood et al. | |
| 7,037,254 B2 | 5/2006 | O'Connor et al. | |
| 7,052,167 B2 | 5/2006 | Vanderschuit | |
| 7,070,584 B2 | 7/2006 | Johnson et al. | |
| 7,077,832 B2 | 7/2006 | Fleischmann | |
| 7,093,600 B2 * | 8/2006 | Sorribes | 128/864 |
| 7,108,683 B2 | 9/2006 | Zamierowski | |
| 7,117,869 B2 | 10/2006 | Heaton et al. | |
| 7,128,719 B2 | 10/2006 | Rosenberg | |
| 7,128,735 B2 | 10/2006 | Weston | |
| 7,144,390 B1 | 12/2006 | Hannigan et al. | |
| 7,169,151 B1 | 1/2007 | Lytinas | |
| 7,182,758 B2 | 2/2007 | McCraw | |
| 7,195,624 B2 | 3/2007 | Lockwood et al. | |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| D544,092 S | 6/2007 | Lewis | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| D565,177 S | 3/2008 | Locke et al. | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,396,345 B2 | 7/2008 | Knighton et al. | |
| 7,401,413 B1 * | 7/2008 | Nelson | 33/512 |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,422,576 B2 | 9/2008 | Boynton et al. | |
| 7,534,927 B2 * | 5/2009 | Lockwood et al. | 602/46 |

| | | |
|---|---|---|
| 7,723,560 B2 * | 5/2010 | Lockwood et al. .......... 602/45 |
| 2001/0020145 A1 | 9/2001 | Satterfield |
| 2001/0031943 A1 | 10/2001 | Urie |
| 2001/0043943 A1 | 11/2001 | Coffey |
| 2002/0016577 A1 | 2/2002 | Ohmstede |
| 2002/0108614 A1 | 8/2002 | Schultz |
| 2002/0143286 A1 | 10/2002 | Tumey |
| 2002/0151836 A1 | 10/2002 | Burden |
| 2002/0161346 A1 | 10/2002 | Lockwood et al. |
| 2002/0198504 A1 | 12/2002 | Risk, Jr. et al. |
| 2003/0078532 A1 | 4/2003 | Ruszczak et al. |
| 2003/0093041 A1 | 5/2003 | Risk, Jr. et al. |
| 2003/0181850 A1 | 9/2003 | Diamond et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0073151 A1 | 4/2004 | Weston |
| 2004/0093026 A1 | 5/2004 | Weidenhagen et al. |
| 2004/0113309 A1 | 6/2004 | Thompson, Jr. et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0243073 A1 | 12/2004 | Lockwood et al. |
| 2004/0249353 A1 | 12/2004 | Risks, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0107756 A1 | 5/2005 | McCraw |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |
| 2005/0288691 A1 * | 12/2005 | Leiboff .......... 606/151 |
| 2006/0015087 A1 | 1/2006 | Risk, Jr. et al. |
| 2006/0025727 A1 | 2/2006 | Boehringer et al. |
| 2006/0029650 A1 | 2/2006 | Coffey |
| 2006/0039742 A1 | 2/2006 | Cable, Jr. et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz et al. |
| 2007/0021697 A1 | 1/2007 | Ginther |
| 2007/0027414 A1 | 2/2007 | Hoffmann et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0066946 A1 | 3/2007 | Haggstrom et al. |
| 2007/0078366 A1 | 4/2007 | Haggstrom et al. |
| 2007/0078432 A1 | 4/2007 | Halseth et al. |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2007/0219513 A1 | 9/2007 | Lina et al. |
| 2007/0225663 A1 * | 9/2007 | Watt et al. ............ 604/313 |
| 2007/0233022 A1 | 10/2007 | Henley et al. |
| 2008/0011667 A1 | 1/2008 | Ruschke |
| 2008/0071235 A1 | 3/2008 | Locke et al. |
| 2008/0082059 A1 | 4/2008 | Fink et al. |
| 2008/0103462 A1 | 5/2008 | Wenzel et al. |
| 2008/0132819 A1 | 6/2008 | Radl et al. |
| 2008/0167593 A1 | 7/2008 | Fleischmann |
| 2008/0183233 A1 | 7/2008 | Koch et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2009/0234313 A1 * | 9/2009 | Mullejeans et al. .......... 604/338 |
| 2009/0264805 A1 * | 10/2009 | Davis et al. .......... 602/43 |
| 2010/0010458 A1 * | 1/2010 | Sherman .......... 604/307 |

FOREIGN PATENT DOCUMENTS

| | | |
|---|---|---|
| DE | 43 06 478 | 9/1994 |
| DE | 295 04 378 U1 | 10/1995 |
| EP | 0 358 302 | 3/1990 |
| EP | 1 088 569 | 4/2001 |
| EP | 1 219 311 | 7/2002 |
| EP | 0 853 950 B1 | 10/2002 |
| GB | 488 232 | 7/1938 |
| GB | 1 415 096 | 11/1975 |
| GB | 2 195 255 A | 4/1988 |
| GB | 2 235 877 A | 3/1991 |
| GB | 1 549 756 | 3/1997 |
| GB | 2 307 180 | 5/1997 |
| GB | 2 329 127 | 3/1999 |
| GB | 2 336 546 | 10/1999 |
| GB | 2 344 531 | 6/2000 |
| GB | 2 415 908 | 1/2006 |
| SU | 1 762 940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1990 |
| WO | WO 92/19313 | 11/1992 |
| WO | WO 93/09727 | 5/1993 |
| WO | WO 94/20041 | 9/1994 |
| WO | WO 96/05873 | 2/1996 |
| WO | WO 00/21586 | 4/2000 |
| WO | WO 03/005943 | 1/2003 |
| WO | WO 03/018098 | 3/2003 |
| WO | WO 03/030966 | 4/2003 |
| WO | WO 03/057070 | 7/2003 |
| WO | WO 03/057071 | 7/2003 |
| WO | WO 03/057307 | 7/2003 |
| WO | WO 03/045492 | 8/2003 |
| WO | WO 03/086232 | 10/2003 |
| WO | WO 03/092620 | 11/2003 |
| WO | WO 03/101508 | 12/2003 |
| WO | WO 2004/018020 | 3/2004 |
| WO | WO 2005/009488 | 2/2005 |
| WO | WO 2006/015599 | 2/2006 |
| WO | WO 2006/105892 | 10/2006 |
| WO | WO 2008/020862 | 2/2008 |
| WO | WO 2008/048481 | 4/2008 |

OTHER PUBLICATIONS

B.M. Kostiuchenok, et al., "The Vacuum Effect in the Surgical Treatment of Purulent Wounds," Russian Journal: Vestnik Khirurgii, 1986, Sep. (18-21).

Chardack, et al.,"Experimental studies on Synthetic Substitutes for Skin and Their Use in the Treatment of Burns," vol. 155, No. 1 (128-136).

Chariker, M. E. et al. (eds), "Effective Management of Incisional and Cutaneous Fistulae with Closed Suction Wound Drainage," Contemporary Surgery, vol. 34, Jun. 1989, pp. 59-63.

H. Teder, et al., "Continuous Wound Irrigation in the Pig," Journal of Investigative Surgery, vol. 3 (399-407).

Jeter, Katherine F., et al., "Managing Draining Wounds and Fistulae: New and Established Methods", Chronic Wound Care, 1990, pp. 240-246.

Meyer, M.D., et al., "In Surgery, Medicine and the Specialties A Manual of its Practical Application", Bier's Hyperemic Treatment, Second Revised Edition, W.B. Saunders Company, 1909.

Mulder, G.D, et al., "Clinicians' Pocket Guide to Chronic Wound Repair," Wound Healing Publications Second Edition, 1991.

N.A. Bagautdinov (Kazan), "Variant of External Vacuum Aspiraton in the Treatment of Purulent Diseses of Soft Tissues," UDC 616-002.036 (94-96).

P. Svedman, "A Dressing System Providing Fluid Supply and Suction Drainage Used for Continuous of Intermittent Irrigation," Annals of Plastic Surgery, vol. 17, No. 2, Aug. 1986 (125-133).

Paul Svedman, "A Dressing Allowing Continuous Treatment of a Biosurface," IRCS Medical Science: Biomedical Technology; Clinical Medicine, Surgery and Transplantation, 7, 221 (1979).

Paul Svedman, "Irrigation Treatment of Leg Ulcers," The Lancet, Sep. 3, 1983 (532-534).

Paul Svedman, et al., "Staphylococcal Wound Infection in the Pig: Part I. Course," Annals of Plastic Surgery, vol. 23, No. 3, Sep. 1989 (212-218).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Sherry Stoll, "Energetic Remedies—Cupping: Healing Within a Vacuum," https://www.suite101.com/article.cfm/energetic remedies/74531, Apr. 13, 2005.

W. Fleischmann, "Vacuum Sealing for Treatment of Problematical Wounds", University Surgical Clinic and Polyclinic—Accident Surgery Department, WundForum Spezial—1HW 94.

W. Fleischmann, et al., Vacuum Sealing: Indication, Technique and Results, Emr J Orthop Surg Tramatol (1995) 5:37-40.

Y.N. Usupov, ct al., "Active Wound Drainage," Russian Journal: Vcstnik Khirugii, 1987, Apr. (42-45).

Yu A. Davydov, et al., "Bacteriological and Cytological Assessment of Vacuum Therapy of Purulent Wounds", Vestnik Khirurgii, 1988, Oct. (48-52).

Yu A. Davydov, et al., "Concepts for Clinical Biological Management of the Wound Process in the Treatment of Purulent Wounds Using Vacuum Therapy," Vestnik Khirugii, 1991, Feb., 132-135).

Yu A. Davydov, et al., "Vacuum Therapy in the Treatment of Purulent Lactation Mastitis," Russian Journal: Vesnik Khirurgii, 1986, Sep. (66-70).

Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

Gorica Zivadinovic, et al., "Vacuum Therapy in the Treatment of Peripheral Blood Vessels," Conference Papers of the 5th Timok Medical Days, Majdanpek, 1986 (161-164).

\* cited by examiner

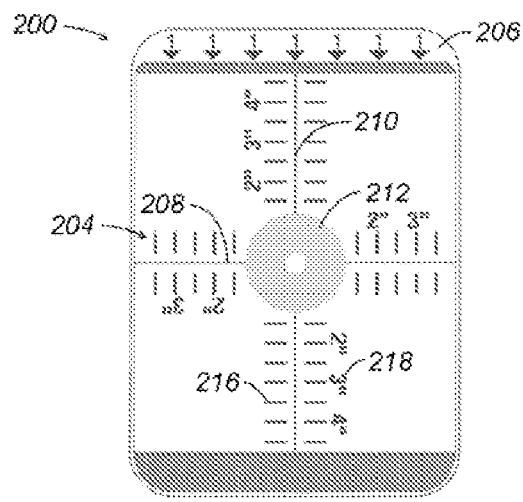 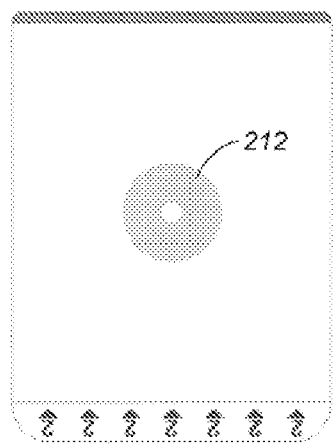
FIG. 4A  FIG. 4B
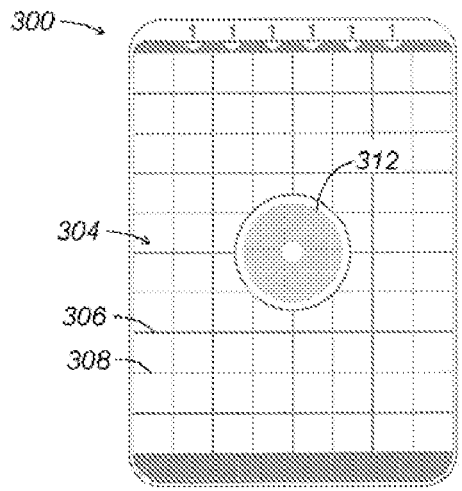 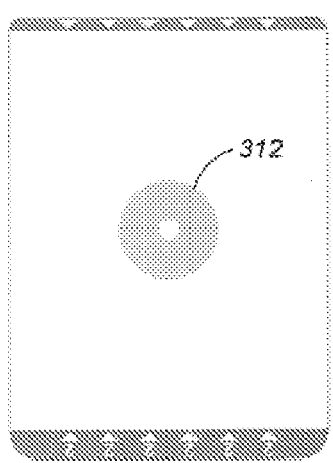
FIG. 5A  FIG. 5B
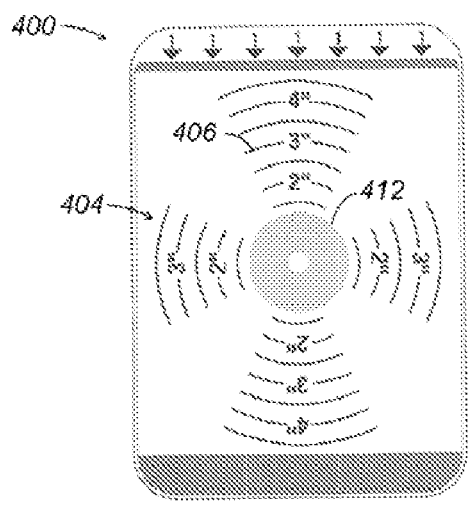 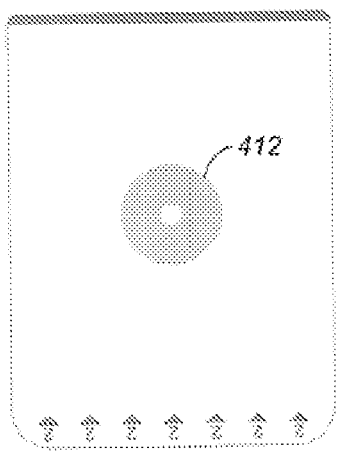
FIG. 6A  FIG. 6B

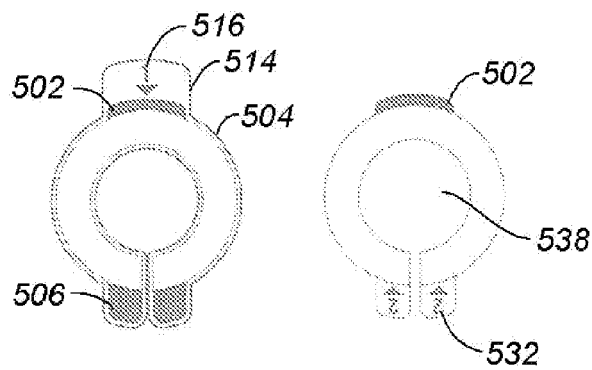
FIG. 7A    FIG. 7B
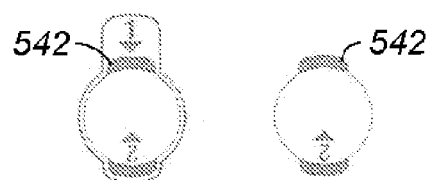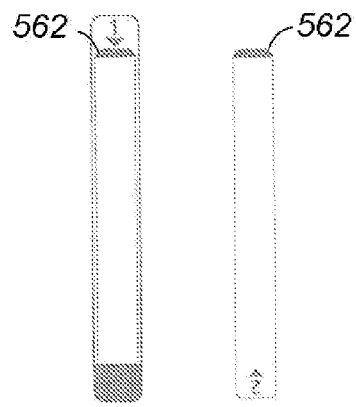
FIG. 8A    FIG. 8B    FIG. 9A    FIG. 9B

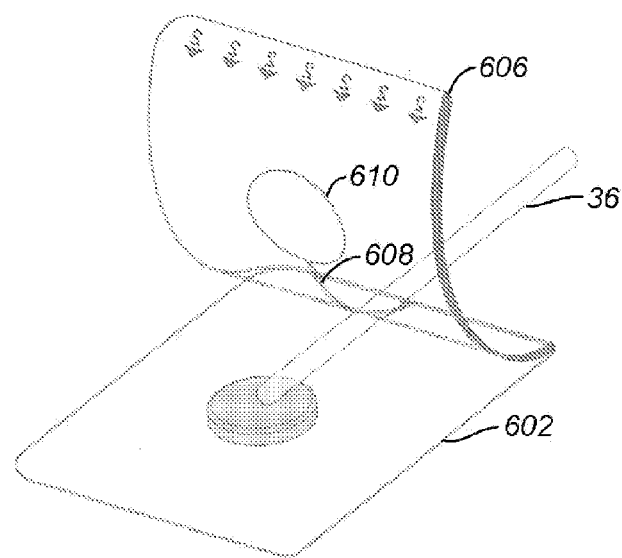
FIG. 10A
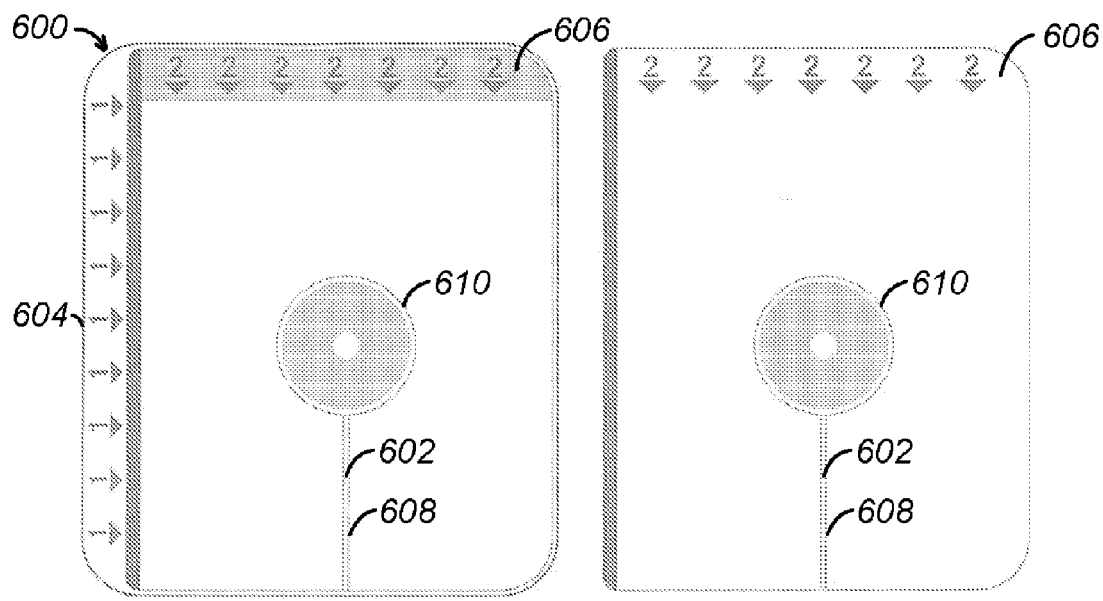
FIG. 10B       FIG. 10C

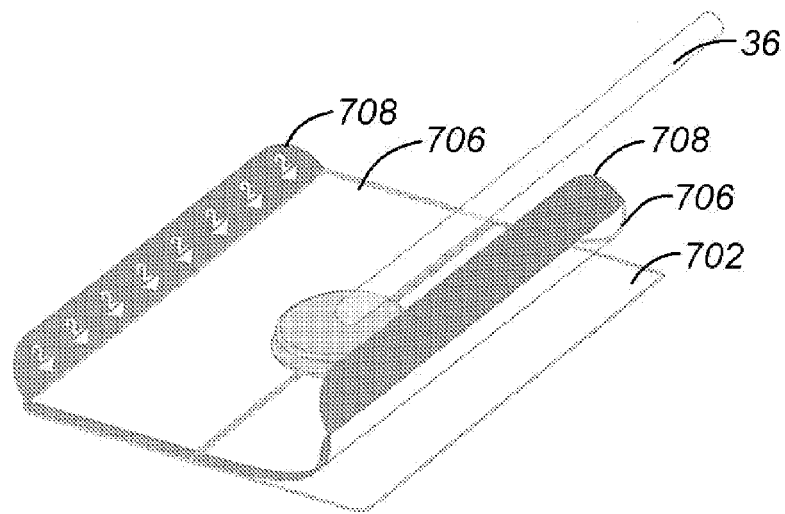
FIG. 11A
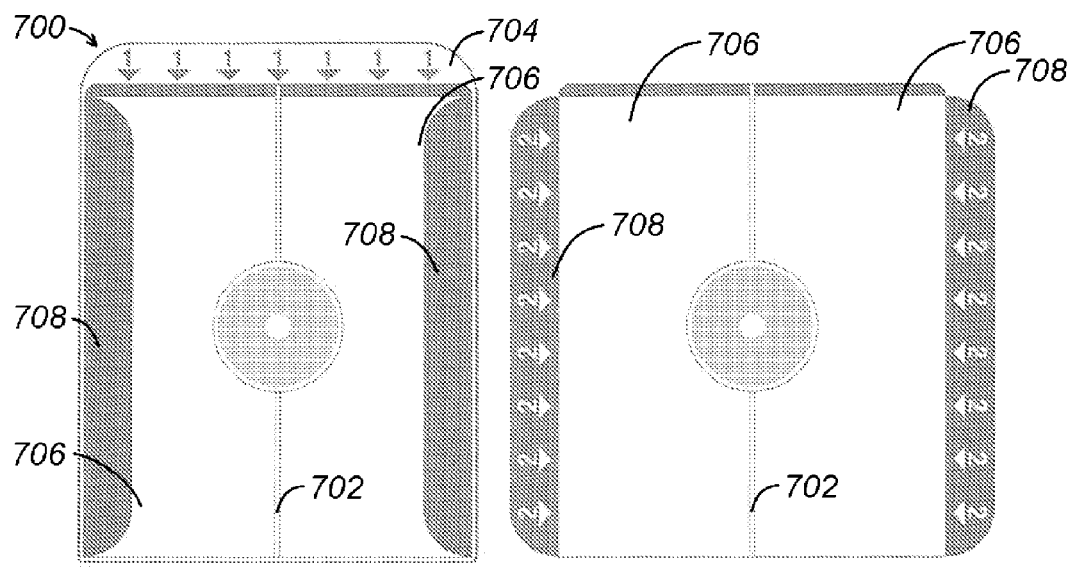
FIG. 11B  FIG. 11C

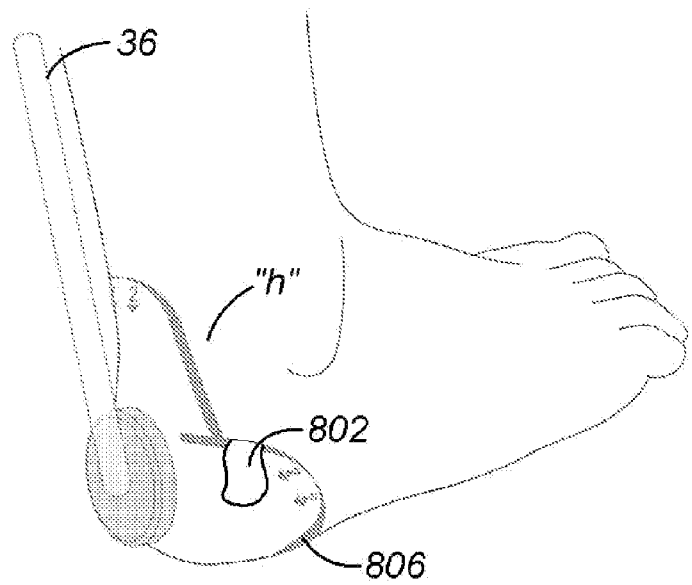
FIG. 12A
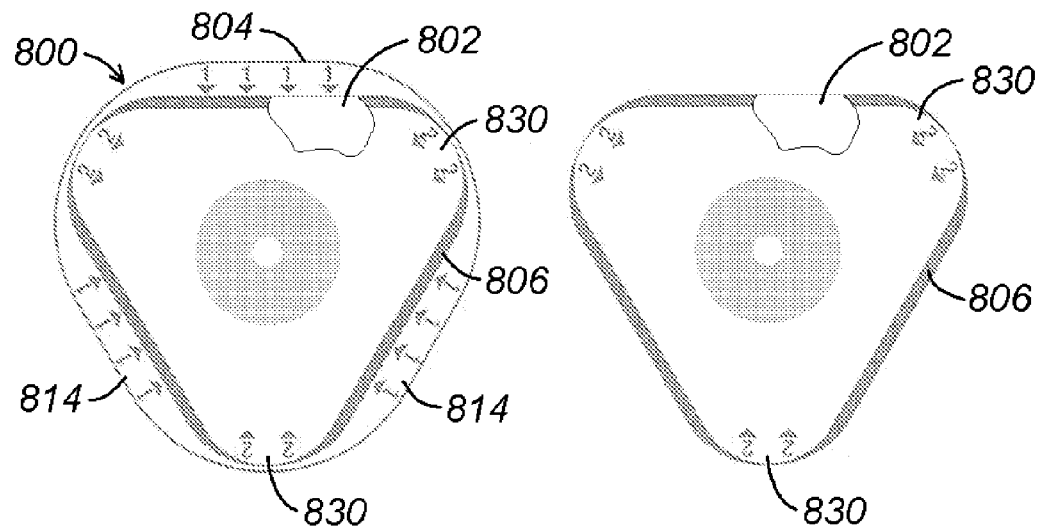
FIG. 12B          FIG. 12C

THIN FILM WOUND DRESSING

BACKGROUND

1. Technical Field

The present disclosure relates generally wound dressings, and in particular to a delivery apparatus for the application of thin film dressings over a wound for use in a treatment such as negative wound pressure therapy.

2. Background of Related Art

Wound dressings are generally placed over a wound to protect and promote healing of the wound. One type of wound dressing consists essentially of a thin membrane of a polymer or similar material, coated on an underside with a pressure-sensitive adhesive. The adhesive may adhere the dressing to healthy skin surrounding the wound such that the dressing provides an effective bacterial barrier to protect the wound from contamination. Because of their extremely elastic nature, thin polymeric film dressings may readily conform to irregular contours of a patient's skin while promoting patient movement and comfort. This type of dressing may also be sufficiently transparent to permit visual inspection of the wound without the need for removing the dressing and exposing the wound to contaminants in the environment.

One technique that may utilize a thin film dressing may be described as negative wound pressure therapy (NWPT). The thin film dressing may be positioned to form a substantially fluid light seal with the skin surrounding the wound to define a reservoir over the wound where a negative pressure may be maintained. The reservoir subjects the wound to a sub-atmospheric pressure to effectively draw wound fluid, including liquid exudates, from the wound with, e.g., a vacuum pump. Vacuum pressure may be applied continuously, or in varying intervals, depending on the nature and severity of the wound. This technique has been found to promote blood flow to the wound area, stimulate the formation of granulation tissue and encourage the migration of healthy tissue over the wound. This type of treatment may subject a thin film dressing to repeated changes of size and shape, taking advantage of the flexibility of the dressing.

The flexibility of a thin film dressing may, however, present difficulties in the application of the dressing to a wound site. For example, the dressing may tend to fold, wrinkle and adhere to itself. To mitigate these tendencies, a delivery layer may be supplied with the dressing to temporarily support the dressing until the dressing is applied. When a thin film dressing is applied as part of an NWPT treatment, additional concerns arise including properly sizing the dressing and appropriately locating a vacuum port relative to the wound. Accordingly, a need exists for a composite dressing and delivery apparatus suitable for use in conjunction with an NWPT treatment.

SUMMARY

A composite wound dressing and delivery apparatus includes a substantially transparent dressing layer having a lower surface that is coated with a pressure sensitive for applying the dressing layer over a wound to define a reservoir in which a negative pressure may be maintained. A substantially transparent backing layer adhered to the lower surface of the dressing layer in a releasable manner, and a vacuum port is centrally located on the dressing layer. The vacuum port is adapted to provide fluid communication between a vacuum source and the reservoir through the dressing layer. A targeting grid associated with either the dressing layer or the backing layer includes regularly spaced reference marks along at least two axes extending from the vacuum port.

The targeting grid may be applied to the backing layer, and may include rule marks associated with two orthogonal axes extending from the vacuum port such that the targeting grid is arranged for Cartesian measurement of a distance to the vacuum port. At least a portion of the rule marks may be associated with numerical markers corresponding to units of a standard measurement system, and the numerical markers may identify a number of the units that is twice a distance from a center of the vacuum port.

The targeting grid may include orthogonal gridlines, including major gridlines and minor gridlines where the major gridlines are adapted to appear more prominent than the minor gridlines. The targeting grid may alternatively include curvilinear rule lines arranged around the vacuum port such the targeting grid is arranged for radial measurement of a distance to the vacuum port.

The apparatus may also include a substantially transparent delivery layer adhered to the upper surface of the dressing layer in a releasable manner. The backing layer may include a first identifier prominently visible thereon and the delivery layer may include a second identifier obscured by the backing layer such that the second identifier is revealed by the removal of the backing layer. The first and second identifiers may thus indicate an order in which the backing layer and delivery layer should be removed from the dressing layer.

The delivery layer may include a slit extending between a central opening and an exterior edge of the delivery layer to permit the delivery layer to be removed from the dressing layer when a vacuum tube is coupled to the vacuum port. The delivery layer may comprise a pair of opposed tabs protruding beyond the extents of the dressing layer. The apparatus also include a dressing layer that is generally triangular in shape.

According to another aspect of the disclosure, a composite wound dressing and delivery apparatus includes a substantially transparent dressing layer having a lower surface and an upper surface. The lower surface is coated with a pressure sensitive adhesive such that the dressing layer may form a fluid tight seal over a wound to define a reservoir in which a negative pressure may be maintained. The apparatus also includes substantially transparent backing layer adhered to the lower surface of the dressing layer in a releasable manner, and a substantially transparent delivery layer adhered to the upper surface of the dressing layer in a releasable manner. A vacuum port is centrally located on the dressing layer, and is adapted to provide fluid communication between a vacuum source and the reservoir through the dressing layer. A targeting grid is associated with the dressing layer, backing layer or the delivery layer, and includes regularly spaced reference marks along at least two axes extending from the vacuum port. Numerical markers correspond to units of a standard measurement system, and identify a number of the units that is twice the distance from a center of the vacuum port.

According to another aspect of the disclosure, a negative wound pressure therapy kit includes a composite wound dressing, a delivery apparatus and a patch. The composite apparatus includes a dressing layer configured for placement over a wound to define a reservoir over the wound in which a negative pressure may be maintained, a backing layer adhered to the dressing layer in a releasable manner and a vacuum port for providing fluid communication through the dressing layer. The vacuum port exhibits a predetermined geometry. The patch includes a patch layer and a backing layer. The patch layer has an opening therein that exhibits a geometry substantially similar to the geometry of the vacuum port.

The kit may further include a filler material adapted for placement within a wound to capture wound exudates, a wound contact layer adapted for placement adjacent the wound to promote unidirectional flow of wound exudates, or a canister adapted for placement exterior to the wound for the collection of wound exudates.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIGS. 4A through 6B are top plan views of alternate embodiments of a composite dressing and delivery apparatus (designated "A"), and corresponding views of the dressing layers prepared for application with backing layers removed (designated "B");

FIGS. 7A through 9B are top plan views of patches for use with a thin film dressing as supplied (designated "A"), and corresponding views of the patches prepared for application with backing layers removed (designated "B");

FIG. 10A is a perspective view of a thin film dressing as applied in an NWPT treatment;

FIGS. 10B and 10C are top plan views of the thin film dressing of FIG. 10A as supplied (designated "B") and as prepared for application (designated "C");

FIG. 11A is a perspective view of a thin film dressing as applied in an NWPT treatment;

FIGS. 11B and 11C are top plan views of the thin film dressing of FIG. 11A as supplied (designated "B") and as prepared for application (designated "C");

FIG. 12A is a perspective view of a thin film dressing as applied in an NWPT treatment; and FIGS. 12B and 11C are top plan views of the thin film dressing of FIG. 11A as supplied (designated "B") and as prepared for application (designated "C").

DETAILED DESCRIPTION OF PREFERRED EMBODIMENTS

Figure 1:
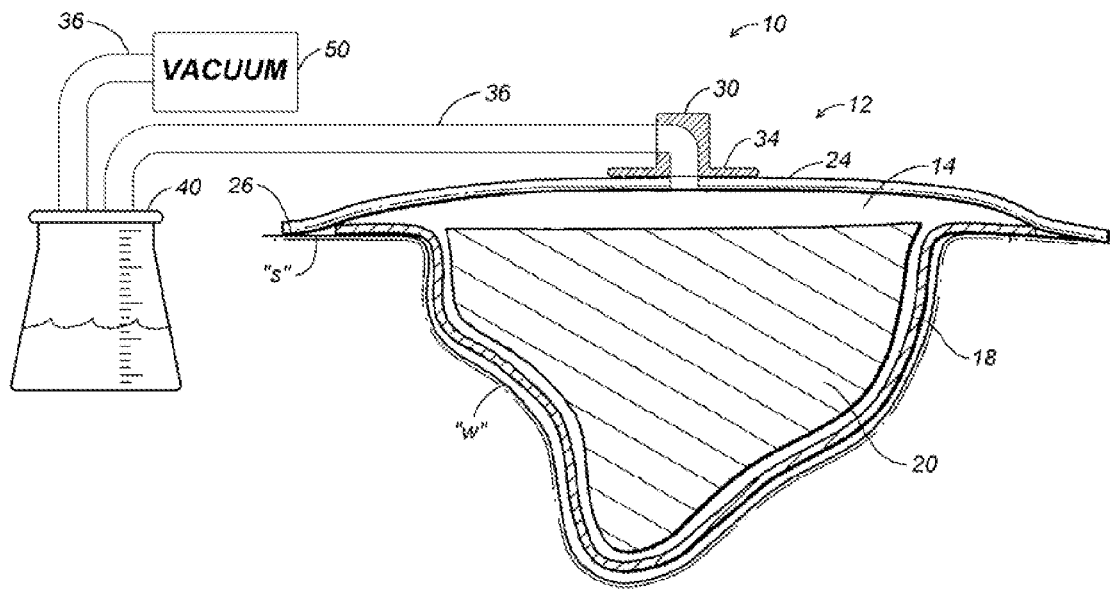
FIG. 1 is a cross sectional view of a thin film wound dressing as applied in an NWPT treatment apparatus.

Referring initially to FIG. 1, a conventional NWPT apparatus is depicted generally as 10 for use on a wound "w" surrounded by healthy skin "s." The NWPT apparatus 10 includes a wound dressing 12 positioned relative to the wound "w" to define a reservoir 14 in which a negative pressure appropriate to stimulate healing may be maintained.

Wound dressing 12 includes a contact layer 18 positioned in direct contact with the bed of wound "w" and may be formed from perforated film material. An appropriate perforated material permits the negative pressure applied to the reservoir to penetrate into the wound "w," and also permits exudates to be drawn through the contact layer 18. Passage of wound fluid through the contact layer 18 is preferably unidirectional such that exudates do not flow back into the wound bed. Unidirectional flow may be encouraged by conical or directional apertures formed in the contact layer 18, or a lamination of materials having absorption properties differing from those of contact layer 18. A non-adherent material may be selected such that contact layer 18 does not tend to cling to the wound "w" or surrounding tissue when it is removed. One exemplary material that may be used as a contact layer 18 is sold under the trademark XEROFORM® and VENTEX® by Tyco Healthcare Group LP (d/b/a Covidien)

Wound filler 20 is positioned in the wound "w" over the contact layer 18 and is intended to allow wound dressing 12 to absorb, capture and/or wick wound exudates. Wound filler 20 is cut to a shape that is conformable to the shape of wound "w," and may be packed up to the level of healthy skin "s," or alternatively, wound filler 20 may overfill the wound "w." An absorbent material such as non-woven gauze, reticulated foam, or alginate fibers may be used for filler 20 to transfer any exudate that migrates through contact layer 18 away from the wound "w". An antimicrobial dressing sold under the trademark KERLIX®AMD by Tyco Healthcare Group LP (d/b/a Covidien), may be suitable for use as filler 20.

Wound dressing 12 also includes a cover layer 24. Cover layer 24 may be positioned over the wound "w" to form a substantially fluid-tight seal with the surrounding skin "s." Thus, cover layer 24 may act as both a microbial barrier to prevent contaminants from entering the wound "w," and also a fluid barrier maintaining the integrity of vacuum reservoir 14. Cover layer 24 is preferably formed from a moisture vapor permeable membrane to promote the exchange of oxygen and moisture between the wound "w" and the atmosphere, and is preferably transparent permit a visual assessment of wound conditions without requiring removal of the cover layer 24. A membrane that provides a sufficient moisture vapor transmission rate (MVTR) is a transparent membrane sold under the trade name POLYSKIN®II by Tyco Healthcare Group LP (d/b/a Covidien) Cover layer 24 may be customized from a composite dressing and delivery apparatus 100 (FIG. 2) as described in greater detail below.

A vacuum port 30 having a flange 34 may also be included in wound dressing 12 to facilitate connection of the wound dressing 12 to fluid conduit 36. The vacuum port 30 may be configured as a rigid or flexible, low-profile component, and may be adapted to receive a fluid conduit 36 in a releasable and fluid-tight manner. An adhesive on the underside of flange 34 may provide a mechanism for affixing the vacuum port 30 to the dressing 12, or alternatively the flange 34 may be positioned within reservoir 14 (not shown) such that an adhesive on an upper side of the flange 34 affixes the vacuum port 30. However it is affixed to the dressing, a hollow interior of the vacuum port 30 provides fluid communication between the fluid conduit 36 and the reservoir 14. Vacuum port 30 may assume various other forms discussed below.

Fluid conduit 36 extends from the vacuum port 30 to provide fluid communication between the reservoir 14 and collection canister 40. Any suitable conduit may be used for fluid conduit 36 including those fabricated from flexible elastomeric or polymeric materials. Fluid conduit 36 may connect components of the NWPT apparatus by conventional air-tight means such as friction fit, bayonet coupling, or barbed connectors. The conduit connections may be made permanent, or alternatively a quick-disconnect or other releasable means may be used to provide some adjustment flexibility to the apparatus 10.

Collection canister 40 may comprise any container suitable for containing wound fluids. For example, a rigid bottle may be used as shown or alternatively a flexible polymeric pouch may be appropriate. Collection canister 40 may contain an absorbent material to consolidate or contain the wound drainage or debris. For example, super absorbent polymers (SAP), silica gel, sodium polyacrylate, potassium polyacrylamide or related compounds may be provided within canister 40. At least a portion of canister 40 may be transparent to assist in evaluating the color, quality or quantity of wound exudates. A transparent canister may thus assist in determining the remaining capacity of the canister or when the canister should be replaced.

Figure 2:
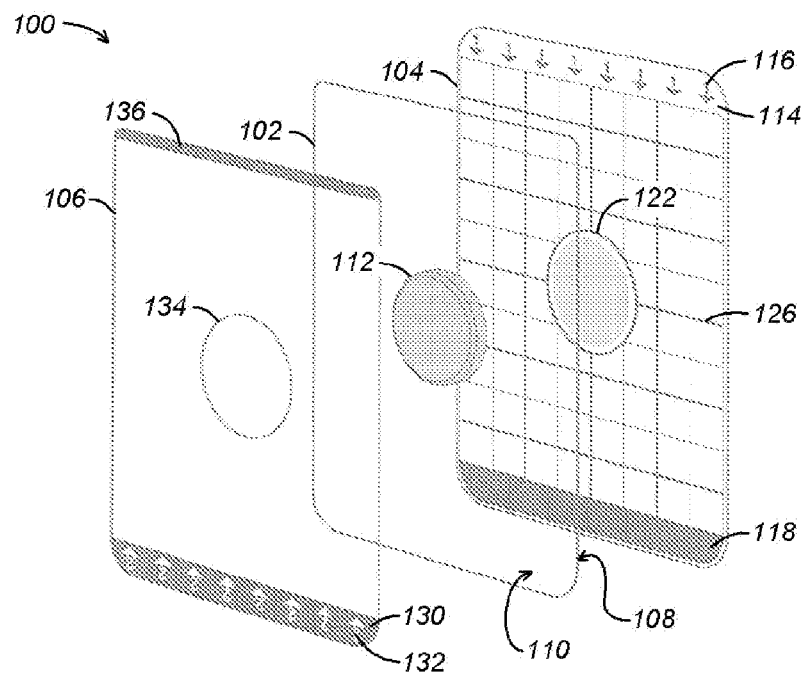
FIG. 2 is an exploded perspective view of a composite dressing and delivery apparatus for the thin film wound dressing of FIG. 1 including a dressing layer, a backing layer and a delivery layer.

Leading from collection canister 40 is another section of fluid conduit 36 providing fluid communication with vacuum source 50. Vacuum source 50 generates or otherwise provides a negative pressure to the NWPT apparatus 10. Vacuum source 50 may comprise a peristaltic pump, a diaphragmatic pump or other mechanism that is biocompatible and draws fluids, e.g. atmospheric gasses and wound exudates, from the reservoir 14 appropriate to stimulate healing of the wound "w." Preferably, the vacuum source 50 is adapted to produce a sub-atmospheric pressure in the reservoir 14 ranging between about 20 mmHg and about 500 mm Hg, about 75 mm Hg to about 125 mm Hg, or, more preferably, between about 40 mm HG and 80 mm Hg. Referring now to FIG. 2, a composite wound dressing and delivery apparatus 100 includes three distinct layers. Centrally located is the dressing layer 102 that may be used to form cover layer 24. Dressing layer 102 is interposed between a backing layer 104 and a delivery layer 106. Each of the three distinct layers 102, 104, and 106 is generally transparent to facilitate placement of the dressing layer 102 over a wound.

Dressing layer 102 may be formed from a variety of thin, transparent, polymeric membranes, such as polyurethane, elastomeric polyester or polyethylene. The thickness of the dressing layer 102 may, for example, be in the range of about 0.8 mils to about 1.2 mils. Thicknesses in this range may permit dressing layer 102 to conform to the contours of a patient's skin surrounding a wound, and accommodate evacuation cycles associated with an NWPT procedure. While the dressing layer 102 may be manufactured in any desired size or shape, the particular geometry of the wound to be treated may prompt customization of each individual dressing layer 102. As provided, dressing layer 102 is generally rectangular having a length of about 6 inches and a width of about 4 inches.

Dressing layer 102 has a lower surface 108 and an upper surface 110. Lower surface 108 is coated with an adhesive to facilitate adherence of the dressing layer 102 to the healthy skin "s" surrounding the wound "w." The adhesive coating should provide firm, continuous adhesion to the skin "s" such that leak paths are not readily formed between the dressing layer 102 and the skin "s" when as reservoir 14 is subjected to the evacuation cycles of an NWPT treatment. The adhesive should also not unduly interfere with the transparency of dressing layer 102, and should peel away from the skin easily when the dressing layer 102 is no longer required.

The adhesive coating also preferably does not interfere with the transmission of moisture vapor through dressing layer 102. To promote enhanced moisture vapor transmission rate (MVTR) of the dressing layer 102, the adhesive coating may be interrupted in some embodiments such that only a periphery of dressing layer 102 is coated to form a seal with the skin "s" leaving a central portion of the dressing layer 102 uncoated. This arrangement is not necessarily preferred since cover layer 102 may be customized to accommodate the particular geometry of an individual wound and an appropriate periphery may not be known at the time of manufacturing. An adhesive coated substantially over the entire lower surface 108 may be selected that exhibits an MVTR equal to that of the film material.

Centrally located on the dressing layer 102 is a vacuum port 112 to facilitate connection to a vacuum tube 38. Vacuum port 112 is depicted schematically and may assume a variety of forms. For example, a structure similar to vacuum port 30 having a flange pre-affixed to dressing layer 102 may be provided along with the composite dressing 100. Alternatively, the vacuum port 112 may consist essentially of a pre-cut hole in the dressing layer 102, or in other embodiments, vacuum port 112 may comprise a marking to indicate a central location of the dressing layer 102 in which an opening may be cut by a clinician after dressing layer 102 is applied over a wound "w."

Backing layer 104 is generally transparent and has a firm but releasable affinity for the adhesively coated lower surface 108 of dressing layer 102. Backing layer 104 covers the lower surface 104 and includes a peripheral region 114 that extends substantially beyond at least one edge of the dressing layer 102. Peripheral region 114 thus provides a gripping surface to facilitate the separation of the backing layer 112 from the dressing layer 102. Peripheral region 114 includes an indicator, such as first numerical indicator 116, printed or otherwise applied thereto. First numerical indicator 116 provides a prominent visual queue to indicate the order in which the three distinct layers 102, 104 and 106 should be separated.

Opposite peripheral region 114, backing layer 104 includes a background region 118 upon which a solid stripe is printed. Background region 118 is less translucent than dressing layer 102 and may be substantially opaque. Also printed on backing layer 104 is a circular reference 122, which is centrally located as to correspond with the location of vacuum port 112 on dressing layer 102. Surrounding the circular reference 122, a targeting grid 126 is printed or otherwise applied with regularly spaced reference lines in two orthogonal directions. Targeting grid 126 may be used to facilitate placement of the vacuum port 108 centrally over a wound "w" by providing a reference for measurement of the wound "w," and by providing a reference for precise cutting or customization of the dressing layer 102.

Delivery layer 106 is adhered to the upper surface 110 of the dressing layer 102 in a releasable manner. Delivery layer 106 is substantially rigid in relation to dressing layer 102 to maintain the dressing layer 102 in a relatively smooth and unwrinkled configuration while the dressing layer 102 is applied to the skin "s." Delivery layer 106 is, however, sufficiently flexible to conform to irregular contours of the skin "s" such that the dressing layer 102 may be pressed onto the skin "s" to form a substantially fluid tight seal therewith.

Preferably, both delivery layer 106 and upper surface 110 are non-adhesive, and may be adhered by heat lamination contact or similar means. A peripheral region 130 of delivery layer 106 overlies dressing layer 102, but is not adhered to dressing layer 102. Peripheral region 130 thus provides a gripping surface to facilitate separation of the delivery layer 106 from the dressing layer 102.

An indicator such as second numerical indicator 132 is positioned on the peripheral region 130 to indicate the order in which the three distinct layers 102, 104 and 106 should be separated. Second numerical indicator 132 is defined by the transparent or relatively transparent text and graphics surrounded by a darker background area of peripheral region 130. The background area of peripheral region 130 may be printed to have an appearance that is substantially similar to the appearance of background region 118 on backing layer 104. In this way, second numerical indicator 132 may be camouflaged or obscured when the backing layer 104 is adhered to the dressing layer 102 and revealed when backing layer 104 is separated from the dressing layer 102.

Delivery layer 106 also includes a central opening 134 to accommodate vacuum port 112 on the dressing layer 102 and a printed boundary 136 opposite peripheral region 130. Printed boundary 136 may be coincident with an edge of the dressing layer 102 to help identify the edge when the delivery layer 106 is adhered to the dressing layer 102.

Figure 3:
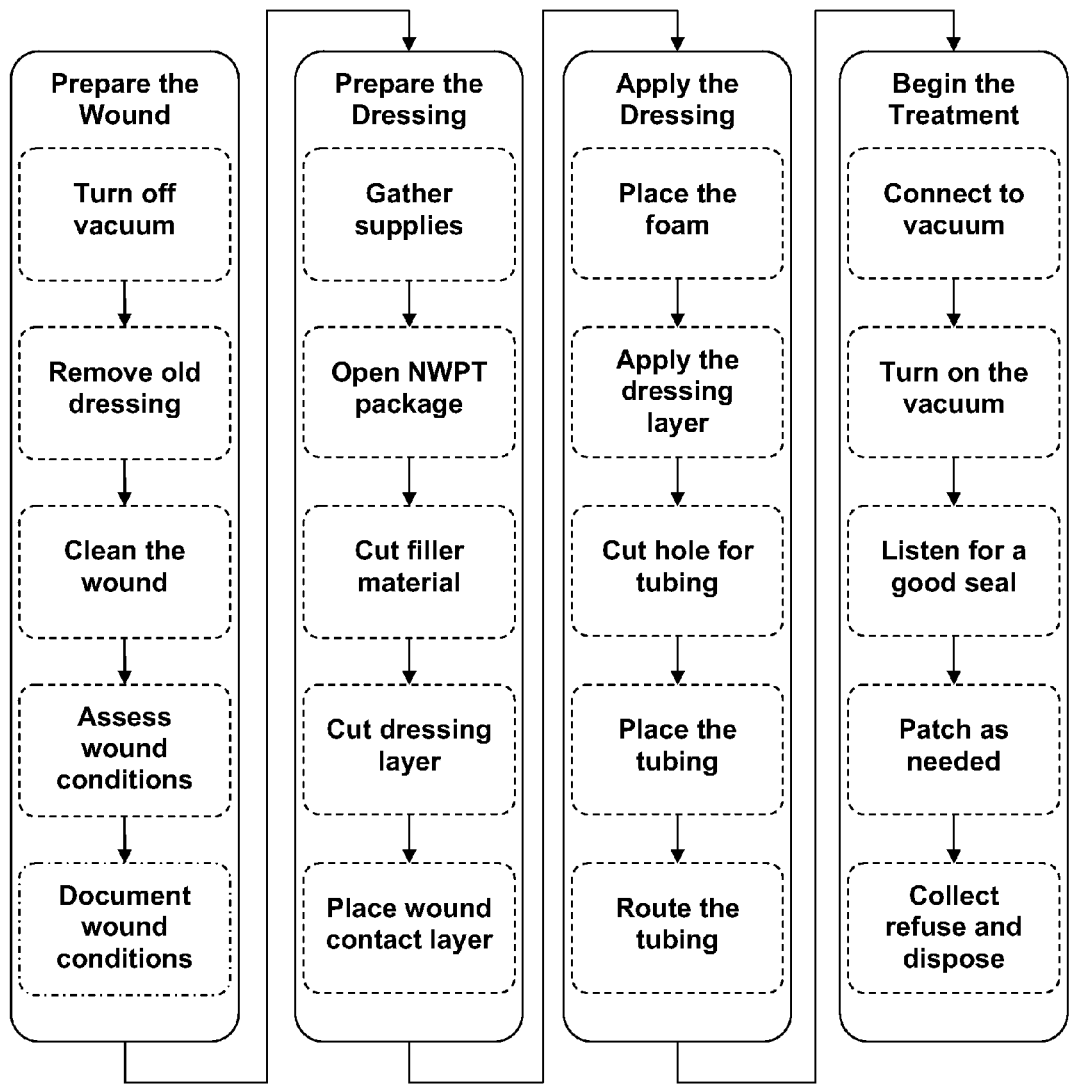
FIG. 3 is a flow diagram describing a process for changing the dressing of FIG. 1.

Referring now to FIG. 3, a process is described for changing a dressing 12 of an NWPT apparatus 10, as depicted in FIG. 1. The process makes use of a composite dressing and delivery apparatus 100 as depicted in FIG. 2, or any of the alternative composite apparatuses discussed below. The procedure includes four major steps, each including a number of sub-steps. Each of the steps and sub-steps may be performed in any suitable order including the order depicted.

In the first major step, the wound "w" is prepared. The vacuum source 50 may be deactivated and the existing dressing 12 may be removed. The wound "w" may be cleaned and wound conditions may then be assessed. The sub-step of documenting the wound conditions may be performed concurrently with the second major step of preparing the dressing, and may be facilitated by any of the composite wound dressing and delivery apparatuses depicted in FIG. 4A through FIG. 6B.

FIG. 4A depicts a composite wound dressing and delivery apparatus 200 having a Cartesian targeting grid 204 printed on a backing layer 206 thereof to assist in documentation of wound conditions. Cartesian targeting grid 204 includes a horizontal axis 208 and an orthogonal vertical axis 210 extending through a central location corresponding with the location of vacuum port 212. Rule marks 216 flank the horizontal and vertical axes 208, 210 in a regularly spaced intervals preferably corresponding to the units of a standard measurement system, e.g. metric or English. Numerical markers 218 may correspond to a number of inches that is twice the distance from a center of vacuum port 212. Composite wound dressing and delivery apparatus 200 may be placed over a wound "w" such that vacuum port 212 is centrally located, and a distance across the wound along in two axes may be noted and documented.

FIG. 5A and FIG. 6A depict alternate composite dressing and delivery apparatuses 300, 400, which may be used in a similar manner to document the size of a wound "w." Composite apparatus 300 includes a targeting grid 304 similar to targeting grid 126 discussed above with reference to FIG. 2. Targeting grid 304 includes major gridlines 306 which are adapted to appear more prominent than minor gridlines 308. Each of the grid lines 306, 308 may correspond to a predetermined unit of measurement and distance from vacuum port 312. Composite system 400 includes a polar or radial targeting grid 404. Radial targeting grid 404 includes curvilinear rule lines 406 arranged around vacuum port 412.

In the second major step, the dressing is prepared. Once supplies have been gathered, an NWPT package (not shown) may be opened. An NWPT package may be provided that includes a sterilized kit including various items used in an NWPT procedure such as a composite wound dressing and delivery apparatus 100, material for wound contact layer 18, material for filler 20 and other items including those described herein below. Once the NWPT package is opened, the packaging material may be used as a clean preparation surface for inventory and organization of the kit components. The packaging material should therefore exhibit a tendency to lie flat and should be sufficient in size to accommodate each of the kit components thereon.

Material may be provided in an NWPT kit for filler 20. The material may be cut to size to allow filler 20 to fill or overfill the wound "w" as described above. The composite system 100 may then be cut appropriate the size of the wound "w." To allow dressing layer 102 to form an appropriate seal with the skin "s," composite system 100 should be cut to permit from about one inch to about one and one half inches of contact between the skin "s" and the adhesively coated lower surface 108 of dressing layer 102 around the wound "w." Cutting the composite system 100 may be facilitated by the targeting grid 126, which provides reference to guide the cut.

Surgical scissors (not shown), may be used to make the cut and may be sterilized or cleaned prior to each use. The scissors need not be included in the NWPT kit. The scissors may also be used to cut wound contact layer 18 to size before it is placed adjacent to the wound "w."

In the third major step, the dressing may be applied to the wound "w." The filler 20 may be placed over the contact layer 18. Often, a portion dressing layer 102 that was cut from composite system 100 in a previous step is used to tack the filler 20 in place.

Next, dressing layer 102 may be applied over the wound "w." The backing layer 104 is first separated to expose the adhesive coating on the lower surface 108 of dressing layer 102. First numerical indicator 116 indicates that the peripheral region 114 may first be grasped to remove the backing layer 104. Once the adhesive is exposed, dressing layer 102 may be pressed onto the skin "s" to form a fluid-tight seal therewith. With backing layer 104 removed, second numerical indicator 132 is revealed as described above. The alternate embodiments depicted in FIGS. 4B, 5B and 6B demonstrate other arrangements that may permit a second numerical indicator to be revealed upon the removal of the respective backing layer. Second numerical indicator 132 indicates that the delivery layer 106 may be separated from dressing layer 102 once the dressing layer 102 has been placed over the wound "w." The delivery layer 106 should readily separate from the upper surface 110 of the dressing layer 102 such that the seal formed around the wound "w" is not disturbed and so as not to cause the patient any undue pain.

If necessary, a hole may be cut in vacuum port 112 to receive fluid conduit 36. Fluid conduit 36 may be placed relative to vacuum port 112 such that the fluid conduit 36 may communicate with reservoir 14. Next, an exposed portion of fluid conduit may be oriented or routed so as not to interfere with patient movement or comfort. Again, a portion of the dressing layer 102 that was cut from composite system 100 in a previous step may be used to secure the fluid conduit 36.

In the fourth major step, treatment of the wound "w" may begin. The fluid conduit 36 may be connected to vacuum source 50 through canister 40. The vacuum source 99 may then be activated to evacuate atmospheric gasses from the reservoir 14. A distinctive sound or audible indicator may indicate whether a proper seal has been achieved over the wound "w." If necessary, any leaks identified may be patched with a portion of the dressing layer 102 that was cut from composite system 100 in a previous step.

Alternatively, a prefabricated patch, such as the patches depicted in FIG. 7A through FIG. 9B, may be used to patch any leaks identified. Each of the patches depicted may be formed from materials similar to those selected for dressing layer 102, and may be provided with a composite delivery apparatus similar to the delivery apparatus provided for dressing layer 102. For example, a patch layer 502, as depicted in FIGS. 7A and 7B, includes a backing layer 504 and a delivery layer 506. Backing layer 504 includes a peripheral region 514 extending beyond an edge of the patch 502. First numerical indicator 516 indicates that peripheral region 514 may be grasped to remove the backing layer 504 and expose an adhesive coating on an underside of patch 502. A second numerical indicator 532 (FIG. 7B) is also thereby revealed. The patch layer 502 may be applied over a leak, and delivery layer 506 may be removed.

Patch layer 502 is shaped such that an opening or interior region 538 has a geometry that is substantially similar to the geometry of the vacuum port 112. Interior region 538 may be open to receive vacuum port 112 therein. Creating a seal around vacuum port 112 may present a challenge, and incorporating a patch layer 502 configured to approximate the particular size and shape of the perimeter of vacuum port 112 into an NWPT kit may be helpful. Opening 538 is substantially circular to accommodate vacuum port 112, but other configurations may be used. For example, a patch (not shown) having a semicircular or other arc shape may be provided.

Patch 542 depicted in FIGS. 8A and 8B has a substantially round geometry and may be provided to patch small leaks in anywhere on the dressing layer 102. Patch 562 depicted in FIGS. 9A and 9B has an elongate geometry and may be provided to patch a leak along an edge of dressing layer 102.

Each of the patches described above may be provided as a kit component in an NWPT package. Having prefabricated patches on hand can ensure the integrity of a fluid tight seal over a wound "w." Also prefabricated patches may be used to tack filler 20 in place in a sterile manner, or to conveniently secure the position of fluid conduit 38. Prefabricated patches may be provided to serve any function that may otherwise be served by a portion of the dressing layer 102 that was cut from composite system 100.

A final sub-step may be to collect and retain any unused components, e.g., patches or portions of dressing layer 102, and to dispose of any refuse. Backing layer 104 and delivery layer 106 each include printing thereon, e.g., the targeting grid 126 or numerical identifiers 116, 132, which can assist in locating these components for disposal.

Referring now to FIG. 10A through FIG. 10C, an alternate embodiment of a composite dressing and delivery apparatus is depicted generally as 600. Composite system 600 includes a dressing layer 602, a backing layer 604 and a delivery layer 606. Delivery layer 606 includes a narrow slit 608 therein extending from central opening 610 to an exterior edge to allow the delivery layer 606 to be conveniently removed after fluid conduit 36 has been routed as depicted in FIG. 6A.

Backing layer 604 includes a peripheral region 614 with a first numerical indicator 616, and a background region 618 positioned along an edge orthogonal to the peripheral region 614. Delivery layer 606 includes a second numerical indicator 632 printed in a darker color than background region 618. Second numerical indicator 632 is thus visible when backing layer 604 is adhered to dressing layer 602, but more prominent when backing layer 604 is removed.

Referring now to FIG. 11A through FIG. 11C, an alternate embodiment of a composite dressing and delivery apparatus is depicted generally as 700. Composite system 700 includes a dressing layer 702, a backing layer 704 and a pair of opposed delivery layers 706. Each delivery layer 706 includes a tab 708 along an edge thereof that protrudes beyond the extents of dressing layer 702. As provided tabs 708 may be folded inwardly as depicted in FIG. 11B. In use, each tab 708 may be folded out to provide a non-adhesive gripping surface that may be handled to place the dressing layer 702 over the wound. Tabs 708 may eliminate a need for gripping an adhesive coating on dressing layer 702, and thereby improve the sealing characteristics of the dressing layer 702 and promote the cleanliness of the wound "w."

Referring now to FIG. 12A through FIG. 12C, another embodiment of a composite dressing and delivery apparatus is depicted generally as 800. Composite system 800 includes a dressing layer 802, a backing layer 804 and a delivery layer 806. Dressing layer 802 is generally triangular in shape such that it may conform to contours of an irregular body part such as a heel "h" as depicted in FIG. 12A. Also, a dressing layer 802 configured with a triangular shape may offer a convenient form to include multiple peripheral regions 814 on backing layer 804, and multiple peripheral regions 830 on delivery layer 806. Multiple peripheral regions 814, 830 may facilitate placement of dressing layer 802 in the event that customizing or cutting the composite system 800 results in the removal of one or more of the peripheral regions 814, 830.

Although the foregoing disclosure has been described in some detail by way of illustration and example, for purposes of clarity or understanding, it will be obvious that certain changes and modifications may be practiced within the scope of the appended claims.

What is claimed is:

1. A composite wound dressing and delivery apparatus comprising:
   a substantially transparent dressing layer having a lower surface and an upper surface, the lower surface coated with a pressure sensitive adhesive such that the dressing layer may form a fluid tight seal over a wound to define a reservoir in which a negative pressure may be maintained;
   a substantially transparent backing layer adhered to the lower surface of the dressing layer in a releasable manner;
   a substantially transparent delivery layer adhered to the upper surface of the dressing layer in a releasable manner;
   a vacuum port centrally located on the dressing layer, the vacuum port adapted to provide fluid communication between a vacuum source and the reservoir through the dressing layer; and
   a targeting grid on either the dressing layer or the backing layer including regularly spaced reference marks along at least two axes extending from the vacuum port,
   wherein the backing layer comprises a first identifier prominently visible thereon and the delivery layer comprises a second identifier obscured by the backing layer such that the second identifier is revealed by the removal of the backing layer, the first and second identifier adapted to indicate an order in which the backing layer and delivery layer should be removed from the dressing layer.

2. The apparatus according to claim 1, wherein the targeting grid is applied to the backing layer.

3. The apparatus according to claim 1, wherein the targeting grid includes rule marks associated with two orthogonal axes extending from the vacuum port such that the targeting grid is arranged for Cartesian measurement of a distance to the vacuum port.

4. The apparatus according to claim 3, wherein at least a portion of the rule marks are associated with numerical markers corresponding to units of a standard measurement system, the numerical markers identifying a number of the units that is twice a distance from a center of the vacuum port.

5. The apparatus according to claim 1, wherein the targeting grid includes orthogonal gridlines, the grid lines including major gridlines and minor gridlines, the major gridlines adapted to appear more prominent than the minor gridlines.

6. The apparatus according to claim 1, wherein the targeting grid includes curvilinear rule lines arranged around the vacuum port such that the targeting grid is arranged for radial measurement of a distance to the vacuum port.

7. The apparatus according to claim 1, wherein the delivery layer comprises a slit extending between a central opening and an exterior edge of the delivery layer to permit the delivery layer to be removed from the dressing layer when a vacuum tube is coupled to the vacuum port.

8. The apparatus according to claim 1, wherein the delivery layer comprises a pair of opposed tabs protruding beyond the extents of the dressing layer.

9. The apparatus according to claim 1, wherein the dressing layer is generally triangular in shape.

10. A composite wound dressing and delivery apparatus comprising:
- a substantially transparent dressing layer having a lower surface and an upper surface, the lower surface coated with a pressure sensitive adhesive such that the dressing layer may form a fluid tight seal over a wound to define a reservoir in which a negative pressure may be maintained;
- a substantially transparent backing layer adhered to the lower surface of the dressing layer in a releasable manner;
- a substantially transparent delivery layer adhered to the upper surface of the dressing layer in a releasable manner;
- a vacuum port centrally located on the dressing layer, the vacuum port adapted to provide fluid communication between a vacuum source and the reservoir through the dressing layer; and
- a targeting grid on any of the dressing layer, backing layer and the delivery layer, the targeting grid including regularly spaced reference marks along at least two axes extending from the vacuum port, and numerical markers corresponding to units of a standard measurement system, the numerical markers identifying a number of the units that is twice the distance from a center of the vacuum port;
- wherein the backing layer comprises a first identifier prominently visible thereon and the delivery layer comprises a second identifier obscured by the backing layer such that the second identifier is revealed by the removal of the backing layer, the first and second identifier adapted to indicate an order in which the backing layer and delivery layer should be removed from the dressing layer.

* * * * *